United States Patent [19]

Keller, Jr. et al.

[11] 4,331,157
[45] May 25, 1982

[54] MUTUALLY NONINTERFERING TRANSCUTANEOUS NERVE STIMULATION AND PATIENT MONITORING

[75] Inventors: John W. Keller, Jr., Miami, Fla.; William E. Bursack, New Brighton; Alan Coombes, Brooklyn Park, both of Minn.

[73] Assignee: Stimtech, Inc., Minneapolis, Minn.

[21] Appl. No.: 167,268

[22] Filed: Jul. 9, 1980

[51] Int. Cl.³ .............................................. A61B 5/04
[52] U.S. Cl. ................................................ 128/419 R
[58] Field of Search ............. 128/696, 697, 702, 704, 128/706, 708, 710, 419 R, 422

[56] References Cited

U.S. PATENT DOCUMENTS

| | | | |
|---|---|---|---|
| 3,824,990 | 7/1974 | Baule | 128/702 |
| 3,897,774 | 8/1975 | Burdick et al. | 128/697 |
| 3,911,930 | 10/1975 | Hagfors et al. | 128/421 |
| 4,105,023 | 8/1978 | Marchese et al. | 128/697 |
| 4,149,527 | 4/1979 | Naylor et al. | 128/697 |
| 4,243,045 | 1/1981 | Maas | 128/696 |

Primary Examiner—William E. Kamm
Attorney, Agent, or Firm—Audley A. Ciamporcero, Jr.

[57] ABSTRACT

Transcutaneous electrical nerve stimulation is applied to the patient, as though electrocardiograph monitoring is not being practiced. The EKG signals are preprocessed through a selective sample and hold module, which performs amplification, comparison with selective frequency and amplitude standards (as by differentiation) and temporary holding of EKG signals at such time as the transcutaneous nerve stimulating pulses are occurring, as sensed against the frequency and amplitude criteria. In the absence of transcutaneous stimulation signals, EKG signals are coupled directly through for conventional EKG processing.

6 Claims, 2 Drawing Figures

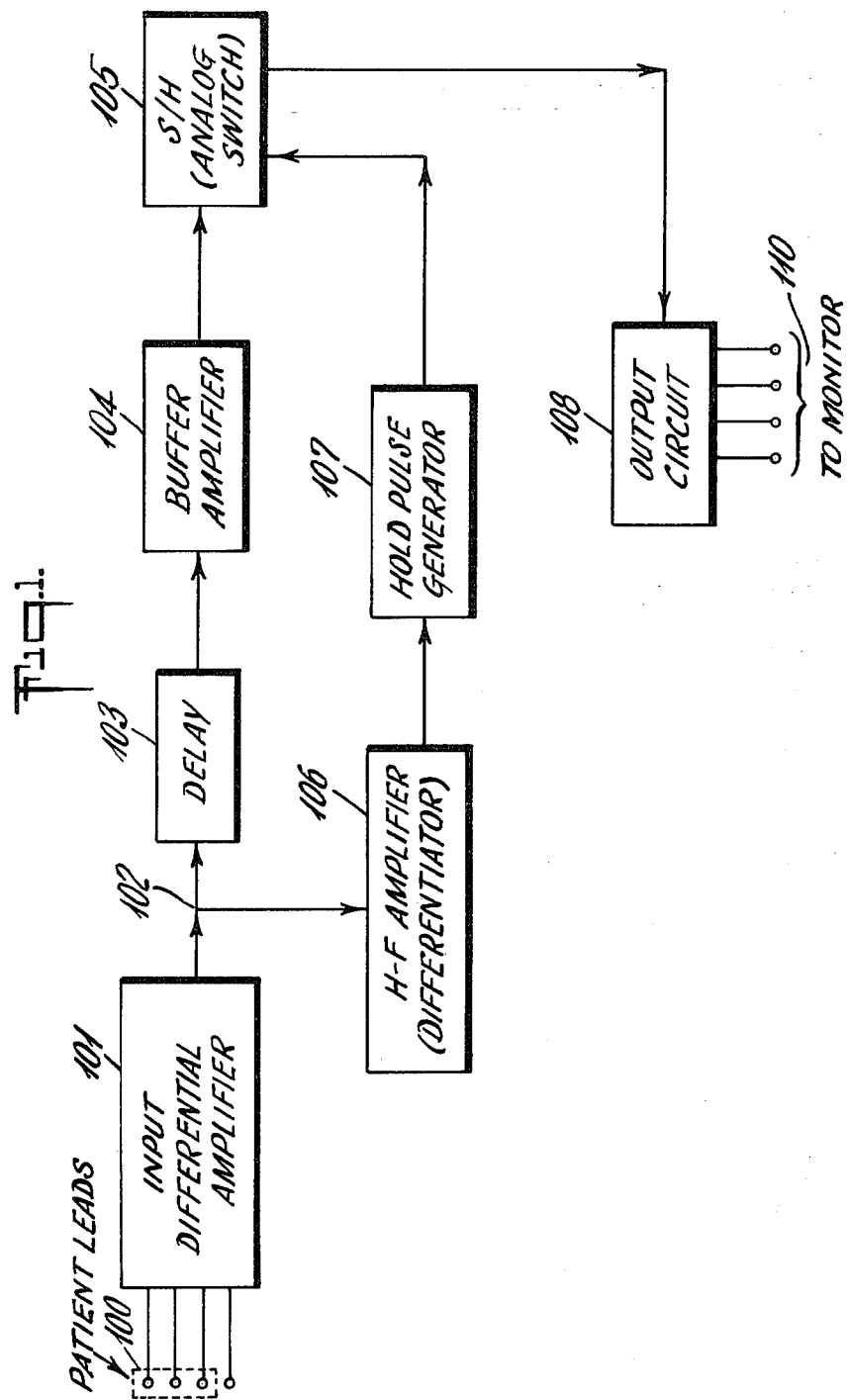

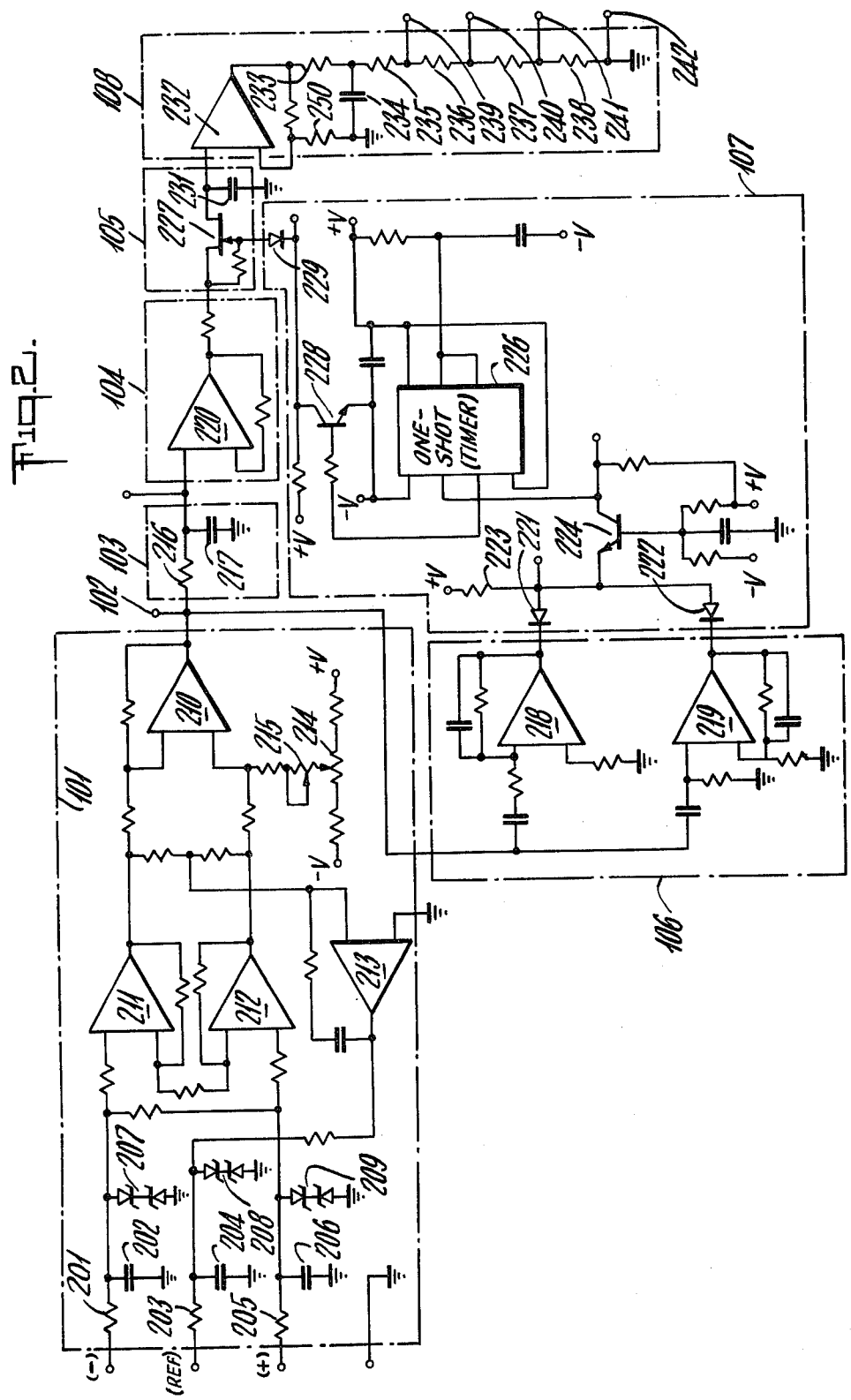

MUTUALLY NONINTERFERING TRANSCUTANEOUS NERVE STIMULATION AND PATIENT MONITORING

FIELD OF THE INVENTION

This invention relates both to the monitoring of patient vital signals, such as by electrocardiograph, and to the application of transcutaneous electrical nerve stimulation to a patient for purposes of pain control. More particularly, it relates to simultaneous, mutually noninterfering conduct of such monitoring and such stimulation.

BACKGROUND OF THE INVENTION AND PRIOR ART

Increasingly, transcutaneous electrical nerve stimulation (TENS), also often referred to as electronic pain control, is finding acceptance as an aid or supplement to anesthesia and/or analgesia. It has been known for some time that transcutaneous stimulation is a useful and effective moderator of post-operative pain (see, for example, U.S. Pat. No. 3,911,930 to Hagfors et al.). More recent investigations indicate that TENS may also have a synergistic interaction with oft used anesthetics and analgesics in a fashion which substantially alleviates pain and discomfort of the patient, while substantially reducing the amount and character of drugs to which the patient must be subjected. In U.S. application Ser. No. 133,211 to Bussey, filed Mar. 24, 1980, there is disclosed a method for utilizing the combination of transcutaneous nerve stimulation with anesthetics and analgesics during surgery. That application also features the utilization of electronic pain control apparatus in such a manner and of such a character as the electrodes which are positioned on the patient before and during surgery, may be left in place for utilization for alleviating pain during the post-operative period.

Quite commonly, however, both during the operative procedure and during the recovery period thereafter, the surgeon, the anesthesiologist, and other attending physicians and nurses have need continuously to monitor certain vital signs of the patient, such as cardiac function. The conventional mode of monitoring cardiac function is utilization of the electrocardiograph (EKG) through the positioning of several sensing electrodes on the patient, in known fashion, thereby to detect induced electrical variations proportional to and directly representative of heart activity (i.e. the well-known cardiac PQRST complex).

Problems arise in the simultaneous conduct of transcutaneous electrical nerve stimulation and the likes of EKG monitoring, however, because of the character and frequency spectrum of the EKG signal, in both healthy and ailing patients, and the character and frequency spectrum of electrical signals which are known to be effective for purposes of electronic pain control. Unless some appropriate precaution is taken, the EKG trace during and immediately after each pulsed application of TENS at best will be meaningless, and at worst will provide a false or erroneous indication of patient conditions which in fact are not occurring.

It is accordingly a primary object of the present invention to provide apparatus and methods whereby transcutaneous electrical nerve stimulation may be applied to a patient, either alone or in combination with select anesthetic and analgesic agents, during times in which patient vital signs, such as cardiac function, are being continuously or intermittently monitored.

Problems attendant to mutually interfering signals both generated in treating the patient and sensed in the patient through monitoring, are not new. Indeed, a number of patents purport to deal with such mutual interference problems in the operating theatre, in the intensive care unit, and elsewhere. For example, U.S. Pat. No. 4,117,848 to Naylor discloses the use of a follow and hold circuit to suppress pacer pulses in an EKG monitor. Likewise, U.S. Pat. No. 3,897,774 to Burdick et al., U.S. Pat. No. 4,137,908 to Degonde et al., and U.S. Pat. No. 3,534,282 to Day disclose alternative approaches to mutually noninterfering utilization of heart pacing and EKG monitoring. U.S. Pat. No. 3,716,059 to Welborn et al. describes a cardiac resuscitator including a disposable clamp controlled to inhibit transmission of EKG signals at times when electrical stimulation is being delivered to the patient. Fletcher U.S. Pat. No. 3,910,257 discloses a sample and hold approach to EKG signals, for purposes of monitoring and subsequent coupling to a data acquisition unit.

Each such prior art approach, is less than preferred for the electronic pain control situation, not to mention for their own purported situation, for a variety of reasons. Not the least of these is the need externally to interconnect the respective signal generating and signal sensing units; also they tend to sense signals in a fashion which is counterproductive to overriding TENS objectives, or which involves specialized and elaborate synchronization and signal processing requirements, or which is so especially adapted to the application disclosed in the patents that there results little of relevance to the TENS-EKG situation.

SUMMARY OF THE INVENTION

The present invention is based on the proposition that, due to the inherent character of effective transcutaneous electrical nerve stimulation signals and their transit through the body, and the inherent character of cardiac function as represented by electrocardiograph signals, suitable monitoring of the EKG signals, and suitable application of select, predetermined amplitude and frequency criteria thereto, will permit the detection of the occurrence of TENS signals directly from the EKG signals. During such periods of TENS "interference", the EKG signals which occurred just prior to such sensing are sampled and held, extending also for a desired period after the occurrence of the stimulation pulse.

Thus, in accordance with the principles of the present invention, transcutaneous electrical nerve stimulation is applied to the patient, utilizing placement and pulsing of TENS stimulating electrodes in such fashion as may be safe and effective, virtually irrespective of the conduct of EKG monitoring. No interconnection is required between the TENS unit and the EKG monitoring. Likewise, the EKG electrodes are positioned as desired, and the EKG leads are coupled to a unit embodying the principles of the present invention and situated intermediate the leads and the EKG processing unit.

In a unit embodying the principles of the present invention in preferred fashion, EKG patient leads are first coupled to an input differential amplifier featuring appropriate amplification, filtering, and common mode rejection functions. The signal path then is bifurcated, one arm of which includes a delay circuit followed by a sample and hold circuit. The other path of the bifurcation first includes a high frequency differential amplifier which in preferred form performs a differentiation function, whereby amplitude and frequency criteria may be applied simultaneously based on time rate of change of the EKG signal. In this fashion, it is possible to discriminate between the stimulating pulse and certain similarly composed aspects of the electrocardiograph signal, such as the R-wave. For such signals which exceed the joint frequency/amplitude criteria, indicating occurrence of a stimulating pulse, a "hold pulse" generator is activated, typically a one shot timer circuit which operates a sample and hold switch located at a terminating junction of the bifurcated paths. An EKG signal which occurred just prior to initiation of the stimulating pulse thereby is held for an appropriate time, determined by the duration of the hold pulse, whereafter the normal EKG channel passes subsequent signals. In a preferred form of the present invention, the sample and hold operation extends not only for the actual duration of the associated transcutaneous electrical nerve stimulation pulse, but furthermore for a time thereafter appropriate to insure that "clean" EKG signals will once more be sensed. Finally, appropriate attenuation is utilized to scale the remaining signal (i.e. the EKG signal) for introduction into a conventional EKG amplifier and monitor.

It is a foremost feature of the present invention that the occurrence of the interference (i.e. TENS) signal is detected in the true (i.e. EKG) signal, with no additional connection required from the TENS unit for synchronization of sampling/holding operations. This provides considerable advantage and freedom in selection of TENS units with disparate operational characteristics, and in application of any given such unit to the patient free of inteconnection and mechanical or electrical interface connections or constraints.

DESCRIPTION OF THE DRAWINGS

FIG. 1 shows a block diagrammatic version of a module embodying the principles of the present invention and adapted to be incorporated intermediate conventional electrocardiograph electrodes, and a conventional electrocardiograph amplifier/monitor/plotter.

FIG. 2 shows a detailed schematic which embodies the block diagrammatic version of FIG. 1 in a preferred form.

BEST MODE FOR CARRYING OUT THE INVENTION

In the ensuing discussion, little attention is accorded the actual mechanism of application of transcutaneous stimulating electrodes to a patient, or to any precise apparatus for generating the TENS signals and transmitting them to the electrodes. It is to be understood that the art of transcutaneous electrical nerve stimulation for pain control is by now reasonably well developed, and that numerous units are commercially available from a variety of sources, (including the assignee hereof), involving electronics and electrode construction of varying degrees of sophistication and expense. Indeed, the preponderance of commercial units operate within the constraints set forth in the aforementioned Hagfors et al. patent. To the extent necessary, that patent is incorporated by reference herein for purposes of completing the instant disclosure, including provision of illustrative circuitry, specification of TENS wave form parameters, and positioning of electrodes on the patient.

In accordance with the principles of the present invention, the body of the patient serves as an interconnection between the TENS unit and the electrocardiograph, with the interaction of TENS and EKG being sensed by EKG electrodes, then being appropriately processed intermediate the electrocardiograph sensing electrodes and an electrocardiograph system which preferably, although not necessarily, is one of common commercial pedigree. It is also to be understood that the positioning of EKG electrodes on the patient is, in accordance with the principles of the present invention, the same as would be employed in accordance with conventional EKG methods absent the application of electronic pain control.

Referring, then, to FIG. 1, patient leads are shown at 100, it being understood that such leads are appropriately connected, as is known in the art, to suitably positioned EKG sensing electrodes. The EKG signals are coupled, by the leads, to an input differential amplifier 101. Generally, the amplifier 101 employs a high input impedance, high common mode voltage capability, and very high common mode rejection. In this respect, the differential amplifier 101 involves high frequency suppression networks and pulse suppression networks, offset adjustment, and common mode rejection adjustment. At amplifier output node 102, the signal path bifurcates, and the signals from amplifier 101, which still include both EKG and TENS signals (when the latter occur) are coupled both to a delay unit 103 and to an amplifier-differentiator 106. The signal path through delay element 103 and buffer amplifier 104 is the principal signal path, and the delay 103 is provided to compensate for time taken by information processing in the alternative path, which includes a differentiator 106 and a generator of holding pulses 107. Hence, EKG signals normally pass from amplifier 101, through delay unit 103 and amplifier 104, through a switch 105 and to output circuitry 108, so long as no TENS signals are superimposed over the EKG signals. Typically, the output circuit 108 involves attenuation in order to scale the EKG signals into the range commonly acceptable to EKG monitors, designated at 110. The differentiator 106 and generator 107 serve to detect the presence of TENS signals in the EKG waveform, and when such signals are detected, to issue a holding pulse at 107 which energizes the sample and hold switch 105 to interrupt the continuing coupling of EKG signals to the output circuit 108, such holding continuing an appropriate time after the TENS signal pulse has ceased. Such holding time is in essence established by the duration of the holding pulse issued by generator 107.

In accordance with the principles of the present invention, the amplifier/differentiator 106 involves sections, generally parallel to one another, for respective processing of positive and negative transitions of signals from node 102, the subsequent combination thereof, and level shifting and/or amplification of signals above a certain level (corresponding to TENS signals but excluding any aspects of EKG signals). Thus, the evaluation of the derivative of combined EKG/TENS signals (i.e. utilization of the time rate of change, or slope) provides an effective joint amplitude and frequency criterion for discrimination of TENS signals from EKG signals. Level sensitive amplification of the derivative permits the hold pulse generator 107, embodied as a one shot/timer circuit, only to fire a hold pulse upon receipt of an input signal (i.e. amplitude processed time derivative of a signal from node 102) which is a TENS signal (or other spurious signals), but not any aspect of the cardiac function signal represented by the EKG trace. It will be understood that frequency and amplification criteria may be established in manners other than utilization of time derivatives and level sensitive amplification as described in conjunction with FIG. 1.

The operation of the illustrative embodiment set forth in block diagrammatic form in FIG. 1 may perhaps be better understood upon consideration of the circuit schematic set forth in FIG. 2, which in fact exemplifies a preferred embodiment of the principles of the present invention. In FIG. 2, each of the functional blocks 101 through 108, inclusive, of FIG. 1 is provided as a phantom enclosure for detailed circuitry which performs the operations attributed to the corresponding functional element of the FIG. 1 embodiment.

The electrocardiograph leads, designated 100 in FIG. 1, are shown in FIG. 2 as respective negative, reference, positive, and ground connections. The former three are connected to respective RC high frequency suppression networks 201-202, 203-204, and 205-206. Also, each is coupled to a pulse suppression network defined by respective diode pairs 207, 208, and 209. Amplifiers 210, 211, and 212, considered together with their respective feedback, biasing, and interconnection components, jointly form a differential amplifier. Offset adjustment is provided by variable resistor 214, and common mode rejection adjustment is provided by variable resistor 215. As noted, the output signals from amplifiers 211 and 212 are coupled to the input of a differential amplifier 210, and amplifier 213 feeds common mode signal, in inverse phase, back to the patient (i.e. via pulse suppression network 208 and high frequency suppression network 203-204), for improved common mode rejection.

Signals at node 102, at which the signal path divides, include EKG signals and, sometimes, TENS signals. The output of amplifier 101, along the principal signal path, is first coupled to the delay network 104, defined by resistor 216 and capacitor 217, and then to an amplifier 220, with associated feedback and biasing circuitry. The output of buffer amplifier 104 is coupled to, and as appropriate, through, a junction FET switch 227 and to a holding capacitor 231. The ability of JFET 227 to pass further signals from amplifier 220 on to capacitor 231 and therebeyond is dependent on the presence or absence of TENS signals in the EKG signals, as detected by high frequency amplifier 106 and coordinated operation of hold pulse generator 107.

As shown, signals from node 102 are coupled to a pair of amplifier sections 218 and 219, the former of which 218 processes positive transitions of any TENS signals present and the latter of which 219 processes negative transitions. Outputs of the amplifiers 218 and 219 are combined by diodes 221 and 222 and resistor 223, and then delivered to a level sensitive amplifier 224 for appropriate level shifting and gain. The combined operation of amplifiers 218 and 219 and the combination of signals therefrom at diodes 221 and 222 and resistor 223 develops a signal proportional to the time derivative of the signal at node 102; the amplitude of that derivative, when adequate to energize transistor 224, corresponds to detection of a TENS signal in the EKG waveform. Appropriate biasing circuitry for transistor 224 establishes this precise level. As appropriate, transistor 224 energizes a one shot circuit preferably embodied by a timer of the type commonly known as a "555" timer, with appropriate interconnection as shown. The one shot 226 drives the switch 227 through transistor 228 and diode 229.

Thus, when TENS signals are detected at 106 and 107, the switch 227 ceases to conduct, and the voltage on capacitor 231 immediately prior to such cessation, continues to be held and coupled to the EKG monitor. The duration of the holding time, established by the one shot 226 together with its associated circuitry suitably embraces the TENS pulse plus a desired time thereafter. When JFET 227 is again rendered conductive, the EKG signals, again free of TENS interference, resume charging and discharging of capacitor 231, and thereby conveying the time varying EKG signal to the output.

Output stage 108 is defined by a buffer amplifier 232 whose gain is adjusted by variation of resistor 250. EKG signals from amplifier 232 are fed to an RC filter 233 and 234, and then to an output resistor network 235-238, inclusive, which are separated by output terminals 239-242 inclusive. The network defined by resistors 235-238 serves first to attenuate the signal to such levels as EKG monitors are adapted to operate, and secondly, to provide an input configuration for the EKG monitor such that the EKG input amplifier's active feedback will operate.

The foregoing has set forth illustrative and preferred embodiments of the principles of the present invention; it is to be understood that numerous alternative embodiments will occur to those of ordinary skill in the art without departing from the spirit or scope of the present invention.

We claim:

1. Apparatus for the conduct on a patient of simultaneous, mutually non-intefering electrocardiograph monitoring (EKG) and transcutaneous electrical nerve stimulation for pain control comprising:
    (a) EKG means for sensing electrical signals from the body of said patient including the cardiac rhythms, said EKG means including electrode means and an EKG data accumulation channel for receiving data from said electrode means;
    (b) transcutaneous nerve stimulation means for direct application to the subject of intermittent pain control pulses of electrical energy;
    (c) means for monitoring said EKG means to detect signals meeting predetermined amplitude and frequency criteria indicative of occurrence somewhere on said patient of transcutaneous nerve stimulation; and
    (d) means, responsive to said means for monitoring, for inhibiting said accumulation channel for a predetermined time after each detection of signals having said predetermined criteria.

2. Apparatus as described in claim 1 wherein said means for monitoring comprises:
    (a) means for developing the time derivative of signals from said EKG means;
    (b) means for providing a reference threshold and for comparing said time derivative with said reference threshold; and
    (c) sample and hold means, activated by said means for comparing, for causing said accumulation channel to maintain EKG data most recently sensed prior to said derivative exceeding said threshold.

3. Apparatus as described in claim 2 wherein said accumulation channel includes time delay means for delaying all signals from said EKG means for a predetermined time delay during simultaneous operation of said means for comparing and, as necessary, activation of said sample and hold means.

4. In a system for passive monitoring of specified patient functions through monitoring of plural sensing electrodes selectively affixed to the patient, apparatus for the application of simultaneous, non-interfering transcutaneous electrical nerve stimulation for pain control, comprising:
  (a) amplifier means, connected to said plural electrodes, for producing a designated monitoring signal;
  (b) means for evaluating said signal relative to predetermined amplitude and frequency criteria; and
  (c) means for coupling said signal to said system for passive monitoring unless said signal meets said criteria, said means for coupling instead then coupling to said system a fixed quantity which is representative of said signal which occurred most recently prior to meeting of said criteria.

5. Apparatus as described in claim 4 wherein said means for evaluating comprises:
  (a) means for developing the time rate of change of said monitoring signal;
  (b) means for developing a predetermined threshold related to select aspects of functions being monitored; and
  (c) means for comparing said time rate of change with said threshold; said means for coupling including sample and hold means activated by said means for comparing upon detection of signals having time rate of change in excess of said threshold.

6. Apparatus as described in claim 4 wherein said means for evaluating comprises:
  (a) first and second amplifier means for developing signals representative of the time derivatives of respective positive going and negative going aspects of said monitoring signal;
  (b) third amplifier means, responsive to said time derivatives, and conditioned to be energized when one of said derivatives exceed a predetermined amplitude; and
  (c) one shot means, controlled by said third amplifier means, for generating an inhibiting pulse of specified duration for said means for coupling.

* * * * *